(12) United States Patent
Jarvis

(10) Patent No.: US 11,951,548 B2
(45) Date of Patent: Apr. 9, 2024

(54) METHOD FOR MANUFACTURING A METAL BASED COMPONENT COMPRISING A PROTRUSION

(71) Applicant: HIPtec AS, Oslo (NO)

(72) Inventor: David Jarvis, Nesbru (NO)

(73) Assignee: HIPtec AS, Oslo (NO)

( * ) Notice: Subject to any disclaimer, the term of this patent is extended or adjusted under 35 U.S.C. 154(b) by 155 days.

(21) Appl. No.: 17/618,780

(22) PCT Filed: Jun. 17, 2020

(86) PCT No.: PCT/EP2020/066797
§ 371 (c)(1),
(2) Date: Dec. 13, 2021

(87) PCT Pub. No.: WO2020/254426
PCT Pub. Date: Dec. 24, 2020

(65) Prior Publication Data
US 2022/0297184 A1 Sep. 22, 2022

(30) Foreign Application Priority Data
Jun. 20, 2019 (EP) ..................................... 19181460

(51) Int. Cl.
*B22F 3/15* (2006.01)
*B22F 7/06* (2006.01)
(Continued)

(52) U.S. Cl.
CPC ................. *B22F 7/08* (2013.01); *B22F 3/15* (2013.01); *B22F 7/064* (2013.01); *B23K 20/02* (2013.01);
(Continued)

(58) Field of Classification Search
None
See application file for complete search history.

(56) References Cited

U.S. PATENT DOCUMENTS 4,124,401 A * 11/1978 Lee .......................... C04B 35/52
51/307
4,380,471 A * 4/1983 Lee ....................... C04B 35/645
51/307
(Continued)

FOREIGN PATENT DOCUMENTS

| CN | 108582502 | 9/2018 |
| EP | 2050561 | 4/2009 |

(Continued)

OTHER PUBLICATIONS

International Search Report and Written Opinion for PCT/EP2020/066797 that is the parent application to the instant application; dated Dec. 8, 2020; 23 pages.

*Primary Examiner* — Devang R Patel
(74) *Attorney, Agent, or Firm* — Harness, Dickey & Pierce, P.L.C.; Anthony G. Fussner

(57) ABSTRACT

The inventive concept relates to method for manufacturing a metal based component comprising at least one protrusion. The method comprises: providing a metal based substrate comprising a surface having at least one cavity; providing a metal based protrusion element comprising a first portion and a second portion, wherein said first portion has a shape that conforms to a shape of the cavity; arranging the first portion of the protrusion element in said cavity such that at least the second portion of the protrusion element protrudes at least 5 mm from a surface of the metal based substrate, to form a substrate comprising a protrusion; placing said substrate comprising a protrusion in a canister such that a void is formed between the canister and the surface of the substrate comprising the protrusion; filling at least a portion of the void with a diamond powder such that the surface of the substrate comprising the protrusion is covered by the inert filler material; removing gas from the interface between said diamond powder and said substrate comprising (Continued)

the protrusion; subjecting said substrate comprising the protrusion to a hot isostatic pressing process for a predetermined time at a predetermined pressure and a predetermined temperature such that said substrate and protrusion element bond metallurgically to each other to form said metal based component comprising said at least one protrusion; removing at least a part of said diamond powder from said metal based component having a protrusion, wherein a melting point of the diamond powder at said predetermined temperature is higher than said predetermined temperature.

12 Claims, 8 Drawing Sheets

(51) Int. Cl.
 B22F 7/08 (2006.01)
 B23K 20/02 (2006.01)
 B33Y 80/00 (2015.01)

(52) U.S. Cl.
 CPC ......... *B33Y 80/00* (2014.12); *B22F 2302/406* (2013.01)

(56) References Cited

U.S. PATENT DOCUMENTS

2014/0334106 A1* 11/2014 Prest ..................... F28F 21/087
 165/185
2016/0187080 A1* 6/2016 Remsburg .............. B23K 20/24
 228/115

FOREIGN PATENT DOCUMENTS

| | | | | | |
|---|---|---|---|---|---|
| GB | 2147011 | A | * 5/1985 | ................ | B22F 3/15 |
| GB | 2562533 | A | * 11/2018 | .............. | B22F 10/20 |
| JP | H01141882 | | 6/1989 | | |
| JP | H05148021 | | 6/1993 | | |
| WO | WO87/06842 | | 11/1987 | | |

* cited by examiner

METHOD FOR MANUFACTURING A METAL BASED COMPONENT COMPRISING A PROTRUSION

This patent application is a U.S. national stage filing under 35 U.S.C. § 371 of PCT International Application No. PCT/EP2020/066797 filed Jun. 17, 2020 (published as WO2020/254426 on Dec. 24, 2020), which, in turn, claims priority to and the benefit of European application No. 19181460.7 filed Jun. 20, 2019. The entire contents of these applications are incorporated herein by reference.

TECHNICAL FIELD

The present invention relates to a method for manufacturing a metal based component comprising at least one protrusion; and to a metal based component comprising at least one protrusion.

BACKGROUND

Metal based components comprising at least one protrusion can be used in various applications and the size and/or composition of such components typically vary a lot between the different applications. The mechanical properties of joint between a base segment and the protrusion is often of great interest.

One method for preparing metal based components having at least one protrusion is to use various types of machining solutions. However, when using machining it is in general not possible to achieve a protrusion in a first material and a base segment of the component in a different, second material. Furthermore, the possibility to form protrusions having various size, shape and geometry are limited by the size and shape of the machining tools. This leads to that complex geometries may be difficult, and in some cases even impossible to achieve by machining.

Thus, to be able create multi-material components, in particular with protrusions having complex geometries, adhesives and other friction based solutions have been used in the art. However, these solutions generally suffer from poor mechanical properties of the joint, in particular when the component is used in demanding applications.

Therefore, there is a need to improve the current state of the art in order to overcome or at least alleviate the above mentioned problems related to metal based components with protrusions.

SUMMARY

It is an object of the present invention to improve the current state of the art and to mitigate at least some of the above mentioned problems. These and other objects are achieved by a method for manufacturing a metal based component comprising a protrusion according to the accompanying independent claims.

According to a first aspect of the invention, a method for manufacturing a metal based component having a protrusion is provided. The method comprises:
  providing a metal based substrate comprising a surface having at least one cavity;
  providing a metal based protrusion element comprising a first portion and a second portion, wherein said first portion has a shape that conforms to a shape of the cavity;
  arranging the first portion of the protrusion element in said cavity such that at least the second portion of the protrusion element protrudes from a surface of the metal based substrate, to form a substrate comprising a protrusion;
  placing said substrate comprising a protrusion in a canister such that a void is formed between the canister and the surface of the substrate comprising the protrusion;
  filling at least a portion of the void with an inert filler material such that the surface of the substrate comprising the protrusion is covered by the inert filler material;
  removing gas from the interface between said inert filler material and said substrate comprising the protrusion;
  subjecting said substrate comprising the protrusion to a hot pressing process for a predetermined time at a predetermined pressure and a predetermined temperature such that said substrate and protrusion element bond metallurgically to each other to form said metal based component comprising said at least one protrusion;
  removing at least a part of said inert filler material from said metal based component having a protrusion,
wherein a melting point of the inert filler material at the predetermined pressure is higher than said predetermined temperature.

The present invention is based on the realization that by providing an inert filler material covering said substrate comprising a protrusion prior to a high pressure isostatic pressing (HIPping) process, protrusion having various complex geometries may be used. The second portion of the protrusion element may in principle be any kind of complex geometry, exemplified but not limited to those mentioned below.

Furthermore, the use of a HIPping process allows for the substrate and the protrusion element to form a metallurgical bond. More specifically, the metal based sheets bonds to each other metallurgically in a multiaxial manner due to the isostatic pressing. This is different from uniaxial metallurgical bonding as achieved with e.g. uniaxial diffusion bonding. Thus, the inventive method forms a high strength bond between the substrate and the protrusion element, which bond can withstand high mechanical stresses typical for several applications.

The protrusion element can thus be machined independently from the substrate. Thus, the size, shape and geometry of the of the portion element is not limited to those that can achieved when machining from a monolithic substrate.

The substrate may be shaped as sheets or plates, such as e.g. Straight or bent sheets or straight or bent plates, or have any other suitable form allowing provision of at least one cavity on a surface thereof. The surface comprising a cavity need not be flat or level, but may also have curved or bent shape. For example, the substrate may be shaped as in at least one of the following: plates, sheets, foils, forged cubes, discs, or forged discs. The substrate should have a height which allows for the formation of at least one cavity therein. The substrate is preferably a monolithic substrate.

Herein, the term "cavity" refers to a blind hole or blind recess formed in a substrate, such as a monolithic substrate. The size of the opening is typically less than 10 cm wide, such as less than 8 cm wide, less than 7 cm wide, less than 6 cm wide, less than 5 cm wide, less than 4 cm wide, or less than 3 cm wide or less than 2 cm wide.

The cavity may extend in a direction substantially perpendicular to the extension of the surface of the substrate. The inner walls of the cavity may be substantially parallel to each other.

In some examples, at least one inner wall of the cavity should have a lengthwise extension at an oblique or preferably right angle with regard to the surface of the substrate comprising said cavity.

The cavity is typically a blind hole provided in the substrate. The cavity may be provided by drilling, or by other means known to a skilled person in the art. The hole may have a circular opening, and preferably comprise a substantially constant diameter.

The shape of the cavity should be made such that the shape of the first portion of the protrusion element conforms to the shape of the cavity. For example, if the shape of the first portion of the protrusion element is cylindrical, the shape of the cavity is a cylindrical hole having substantially the same, or slightly larger, diameter than cylindrical first portion.

In examples, the substrate comprises a plurality of cavities. The plurality of cavities may be formed on a surface of the substrate in an irregular or regular pattern, such as along a straight line or in a matrix pattern. The distance between the adjacent cavities may preferably be chosen such that the protrusion elements, when positioned in the cavities, do not touch or interfere with their respective function.

Herein, the term "protrusion" refers to an object or a part of a component that protrudes from the surface of substrate material. The width of said protrusion in a dimension perpendicular to the width of the substrate may be less than 10% of width of the substrate. The protrusion may protrude at least 1 cm from the surface of the substrate, such as at least 2 cm from the surface of the substrate, at least 3 cm from the surface of the substrate, at least 4 cm from the surface of the substrate, at least 5 cm from the surface of the substrate or at least 6 cm from the surface of the substrate. The term protrusion may also refer to a component that protrudes at least 5 mm from the surface of the substrate material. The protrusion preferably has a ratio of the height of the protrusion (measured from the surface) to the longest of the width or depth of the protrusion of at least 1:3, such as of at least 1:2, or 1:1, preferably of 2:1. In examples where the protrusion has a substantially circular cross-section, when viewed from above, the protrusion may have a ratio of height of the protrusion to the longest chord of the substantially circular cross-section of at least 1:3, such as of at least 1:2, or at least 1:1, preferably of at least 2:1.

The protrusion element of the present disclosure comprises a first portion shaped to conform to the shape of a cavity in the substrates, and a second portion which, when the first portion is arranged in the cavity, protrudes from the surface of the substrate. The shape of the first and second portions can generally be achieved by machining. A lathe may be particularly advantageous in forming the shape of the first portion. Alternatively, the first and second portion may be manufactured to the selected shape, size and form by means of additive manufacturing (3D-printing).

The second portion of the protrusion element refers to the portion that protrudes from the surface of the substrate when the first portion has been arranged in said cavity. Second portion may preferably comprise a shape selected from a cubic shape, a hook-like shape, a barb-like shape, a tapered shape, a threaded portion, a ball joint, a mushroom shape, a rack-like shape, a tube-like shape, a spring-like shape, a screw-like shape and/or a flange.

The protrusion element may also be produced by means of additive manufacturing, or 3D-printing.

In some examples, the second portion may comprise an attachment element. Herein, the term "attachment element" refers to an element configured to allow an attachment of a second material to the second portion. Herein, the attachment element can be a screw, a threaded portion, a hook, a hole, a barb. Other attachment elements may also be contemplated by a person skilled in the art.

In some examples, the metal based substrate and/or protrusion element comprises a wrought material. The material in either the metal based substrate or the protrusion, or both, may alternatively be a cast material, a material obtainable by additive manufacturing ("3D-printing"), a sintered material or the like. The material of the metal based substrate could be different from the material in the protrusion element. For example, the protrusion element could be obtained by additive manufacturing, while the metal based substrate comprises a wrought material.

The inventive method is equally suitable for the case when the metal based substrate and protrusion element is of the same material, as for the case when they are of different materials.

In some examples, the metal based substrate and/or protrusion element may comprise or consist of iron, steel, stainless steel, nickel, aluminum, copper, titanium, magnesium, bronze, stainless steel, superduplex steel, precious metals e.g. gold or platinum, beryllium, zirconium, cobalt, nitinol, invar or magnesium combinations and/or alloys thereof. The substrate may for example be made solely of metal, or be made from a mixture of metal and another type of material. According to at least one example embodiment of the invention, both the substrate and the protrusion comprises mainly metal. For example, comprises at least 51%, or at least 80%, or at least 90%, or at least 95%, or at least 100% metal.

The substrate and the protrusion element may comprise the same material. The substrate and the protrusion element may also comprise different materials.

The second portion of the protrusion element may form a protrusion in the substrate which protrudes at least 5 mm, such as at least 10 mm or more from the surface of the substrate. The second portion preferably has a ratio of the height of the second portion (measured from the surface) to the longest of the width or depth of the second portion of at least 1:3, such as of at least 1:2, or 1:1, preferably of 2:1. In the case where the second portion has a substantially circular cross-section, when viewed from above, the second portion may have a ratio of height of the second portion to the longest chord of the substantially circular cross-section of at least 1:3, such as of at least 1:2, or at least 1:1, preferably of at least 2:1.

Once the protrusion element has been positioned in the cavity to form a substrate comprising a protrusion, said substrate comprising a protrusion is positioned in a canister. Canisters used for HIPping are known to a person skilled in the art. The substrate comprising the protrusion are positioned inside said canister such that a void is formed between the canister and the substrate.

Filling at least a portion of said void with an inert filler material such that the surface of the substrate comprising the protrusion (and the protrusion itself) is covered by the inert filler material yields several advantageous properties. Firstly, it prevents the protrusions from damaging the canister and vice versa upon application of the predetermined pressure during the HIPping step. Furthermore, it provides for an even pressure distribution around the protrusion element during the subsequent HIPping. This is advantageous in that it enables the use of protrusion elements having complex geometries.

Herein, the term "inert filler material" is intended to denote a material which is inert during the at least during said hot pressing process for said predetermined time at said predetermined pressure and said predetermined temperature. This means that the material does not undergo phase change or does not react with itself, i.e. a filler particle will not melt or bond to another filler particle in the inert filler material during the during the hot pressing process for said predetermined time at said predetermined pressure and said predetermined temperature. The inert filler material may be a particulate material.

Furthermore, the inert filler material is a material which exhibit flow properties, which allows it to be poured into the void during the step of filling, and it may be poured out of said void during the step of removal. The flow properties further allow the material to completely cover and surround the at least one protruding element, such that substantially a whole outer surface of the at least one protruding element in contact with the inert filler material during the subsequent step of HIPping.

Thus, in an example when the second portion of protrusion element comprises an eye hook-like shape, i.e. comprises a through hole, the inert filler material will contact fill and contact also the inner surfaces of said through-hole. Thus, during the HIPping step, the inert filler material will provide a counter-pressure which will allow the protrusion element to keep a net-shape, or near net-shape. Thus, the provision of an inert filler material prevents such through-holes, and other complex geometries, from deforming and/or closing during the HIPping treatment. The size and geometry of the protrusion element can thus be preserved after the step of HIPping.

The inert filler material may be a particulate material.

According to at least one example, the inert filler material is configured to have flow properties.

Another advantage with the filling of the void with an inert filler material is that it eliminates the need for the surface comprising the cavity to be flat. Since the pressure provided in the HIPping step is provided to the protrusion and the substrate via said inert filler material, the surface need not be flat in order to achieve an isostatic pressure distribution. Thus, the protruding element can be joined with a substrate that has a wavy, curved or bent surface.

According to an example of the present invention said step of removing gas from said interface, at least 50%, or at least 60%, or at least 70%, or at least 80, or at least 90% of the gas is removed from said interface compared to prior to the step of removing gas from said interface. In other words, said step of removing gas from said interface, may comprise providing a vacuum, or a partial vacuum, in said interface. Stated differently, said step of removing gas from said interface, may comprise providing an under-pressure in said at least one cavity.

According to at least one example, said step of removing gas from the interface between said inert filler material and the surface of the substrate may comprise the sub-steps of:
  providing at least one gas evacuating aperture in the canister, which gas evacuating aperture is fluidly connected to said surface of the substrate;
  evacuating gas from the interface between said inert filler material and said surface of the substrate via said at least one gas evacuating aperture.

Herby, gas may be removed from said interface between said inert filler material and the surface of the substrate in a relatively straightforward way. Hereby, gas, typically air, can be evacuated from said interface, thus providing a vacuum, or a partial vacuum, within the cavity. In some examples, the gas is removed from said interface to an outside of said cavity by e.g. using a suction device connected to said at least one gas evacuating aperture.

According to at least one example of the invention, said at least one gas evacuating aperture is arranged in the canister surrounding said metal based component and/or in said closing member.

According to at least one example, the shape of said at least one gas evacuating aperture is circular. Alternatively, the at least one gas escaping aperture may be elliptical or simply be described as having a round shape. The at least one gas evacuating may be described as a gas evacuating hole or as a gas evacuating opening. Yet alternatively, the gas escaping aperture may have the shape of a line, e.g. a groove or a slit, or it may have any regular or irregular form. According to one example embodiment, the gas evacuating aperture may have a pre-defined form.

According to at least one example the method comprises the steps of:
  arranging a gas evacuating crimp tube to said cavity and e.g. said metal based component, wherein an opening of said gas evacuating crimp tube covers said at least one gas evacuating aperture; and
  sealing said gas evacuating crimp tube after the step of evacuating said gas from said interface between said inert filler material and said at least one surface of the substrate and prior to the step of subjecting said stack to a hot pressing process.

It should be understood that the term cover here means that the diameter of the opening of the crimp tube, i.e. the inner diameter of the crimp tube, is larger than the corresponding size of the at least one gas evacuating aperture. In other words, the opening of the crimp tube surrounds the at least one gas evacuating aperture.

Thus, gas may be removed from the interface between said incompressible coating material and said at least one inner and/or outer surface portion by evacuating gas from said cavity via said at least one gas evacuating aperture using said gas evacuating crimp tube. Moreover, the crimp tube may be used to test the degree of vacuum at said interface, e.g. by connecting it to a vacuum pump.

According to at least one example of the invention, the predetermined time, the predetermined pressure and the predetermined temperature used during high isostatic pressing is within the ranges of what is normally used within the HIPping industry. For example, the predetermined time may be within the range of 1 h to 12 h, the predetermined pressure may be within the range of 10 MPa to 200 MPa, such within the range of 100 MPa to 200 MPa, and the predetermined temperature may be within the range of 500° C. to 2000° C., such as within the range of from 500° C. to 1300° C. The predetermined time, the predetermined pressure and the predetermined temperature may all vary due to a variety of parameters. For example, they may vary due to the size or the shape of the metal based component which is being manufactured. Further, they may vary due to the material choice, e.g. which metal is being used.

According to at least one example embodiment of the invention, the metal based component having a protrusion is a single-piece metal based component. Thus, during the step of subjecting said substrate comprising a protrusion to a to a hot isostatic pressure process, the substrate and the first portion of the protrusion element bond metallurgically to each other and thereby form a single-piece metal based component.

In some embodiments, said arranging the first portion of the metal based protrusion element in said cavity such that the second portion of the protrusion element protrudes from a surface of the first metal based substrate further comprises arranging said first portion to fit snugly inside said cavity, such that the inert filler material is prevented from entering said cavity, and wherein, after said filling, substantially a whole outer surface of the second portion of the protrusion element is in contact with the inert filler material.

Herein, the term "fit snugly" refers to that the first portion of the protrusion element can be positioned tight and close fitting inside said cavity. Substantially the full surface of the outer walls of the first portion should be in contact with the inner walls of the cavity. In the case of a cylindrical protrusion, a snug fit is typically achieved by providing the first portion with a diameter which is approximately the same but slightly smaller than the diameter of the cavity, which is then also cylindrical.

The snug fit prevents the inert filler material from entering the cavity and provides for a large contact surface between an outer surface of the first portion and an inner surface of said cavity, which strengthens the metallurgical bond formed by the HIPping process.

In some embodiments, said first portion has a cylindrical or quadrangular shape and wherein said cavity has a shape of a cylindrical or quadrangular hole. A snug fit can thus be provided choosing the diameter or side lengths of the first portion such that it is substantially the same, or slightly smaller than the diameter or side lengths of the cavity. A circular cylindrical shape of the cavity may be achieved by drilling a blind hole in the substrate, preferably in a direction perpendicular to a direction parallel extension of the surface of the substrate.

In some embodiments, the inert filler material is an incompressible filler material and wherein said step of removing at least a part of said inert filler material comprises removing at least a part of said incompressible filler material from said metal based component.

Herein, the term "incompressible" refers to a filler material wherein the individual elements making up the filler material (whether in the form of powder, beads and/or prills) are in contact with each other and can withstand compression without fracture when being subject to an external load, such as an external load stemming from the hot pressing process, and more specifically, said predetermined pressure during said predetermined time of said hot pressing process.

In some embodiments said incompressible filler comprising at least diamond powder, and wherein said step of removing at least a part of said incompressible filler comprises removing at least a part of said diamond powder from said metal based component.

Hereby, a powder which is incompressible and which is substantially inert, at least during said hot pressing process for said predetermined time at said predetermined pressure and said predetermined temperature, is provided. Moreover, as diamond powder has flow properties, i.e. it may be poured into said void, and it may be poured out from said void, the handling of the incompressible filler is improved. Thus, according to at least one example embodiment, said diamond powder is configured to have flow properties.

This is in contrast to ceramic filler materials, which typically requires leaching to be removed from the metal based component after the process due to the fact that the ceramic will sinter to form a solid body bonded to the component during the hot pressing process. Diamond powder will not sinter or otherwise react with itself. The use of diamond powder is thus advantageous in that it can significantly alleviates the handling after the hot pressing process, since superfluous diamond powder can be poured out of the canister after the process, due to that the grains of the diamond powder does not react with themselves during the hot pressing process. Moreover, the diamond powder poured out of the canister after the process can readily be reused in a further process as disclosed herein.

According to at least one example, the diamond powder comprises at least 50%, or at least 60%, or at least 70%, or at least 80%, or at least 90%, such as e.g. at least 95%, or at least 99%, such as e.g. 100% of diamond particles, said percentage being weight based.

According to at least one example, said diamond powder comprises at least one of the following materials: zirconia, silicon carbide, tungsten carbide, boron carbide, calcium hexaboride. Such material may be present in the diamond powder such that it corresponds to up to 30%, e.g. between 1% and 25%, or between 5% and 15%, of the weight of the total diamond powder.

Even though the void fraction of diamond powder typically is around 30%, the material characteristics of the diamonds, or the diamond powder characteristics, provide for a more or less incompressible property of the diamond powder, as the crystal facets of different diamond particles in the diamond powder are in contact with each other, and thus withstand compression without fracture when being subject to an external load, such as an external load stemming from the hot pressing process, and more specifically, said predetermined pressure during said predetermined time of said hot pressing process.

It should be understood that the diamond powder is inert in the context of not reacting with itself, i.e. a first diamond particle in the diamond powder will not bond to another diamond particle in the diamond powder during the hot pressing process. However, at least some of the diamond particles which are adjacent a metal surface of the surface of the substrate and/or the second portion of the protrusion element, may react and form a metal carbide layer, such as e.g. Iron Carbide, $Fe_3C$, Titanium Carbide, TiC or Tungsten Carbide, WC, depending on the material of the metal surface. Thus, according to at least one example, the method comprises the step of coating, or forming, surface portions on the outer surface of the protrusion element and the substrate with a metal carbide layer. Hence, an outer surface of said metal based component, may be at least partly covered, or coated, with a metal carbide layer. Such metal carbide layer is typically hard, and thus the internal wall portions of said cavity are more wear-resistant.

In some embodiments, the average grain size of said diamond powder is at least 1 μm, or at least 10 μm, or at least 20 μm, or at least 30 μm and/or wherein the average grain size of said diamond powder is at most 1000 μm or at most 500 μm, or at most 250 μm, or at most 100 μm, or at most 50 μm, or at most 40 μm.

The diamond particles of said diamond powder may vary greatly in size. For example, and according to at least one example embodiment, the diamond powder may comprise at least two different sets with different average powder sizes, a so called bimodal mixture. For example, a first set of the diamond powder may comprise diamond particles having a relatively small average powder size, such as e.g. between 1 micron and 400 microns, and a second set of the diamond powder may comprise diamond particles having a relatively larger average powder size, such as e.g. between 600 microns and 1000 micron. Hereby, the void fraction of the diamond powder may be reduced, as the relatively smaller diamond particles (i.e. the set of finer diamond powder) will fill the gaps between the relatively larger diamond particles (i.e. the coarser diamond powder). The average powder size between the first set and the second set may e.g. vary by at least a factor of 2. According to at least one example embodiment, further sets with different average powder size may be present in the diamond powder to provide a so called multimodal mixture.

It should be noted that the term "powder size" may be referred to as "particle size", i.e. said average powder size of said diamond powder may be referred to as an average particle size of said diamond powder.

The powder size may be determined by means of sieving and preferably into tight fractions with respect to size, e.g. by using two or more sieves. Such means are known to a person skilled in the art and are commonly referred to as "mesh".

In one example, the powder size has been determined by sieving through two consecutive US mesh sizes 400 and 500 (400/500 US), which yields powder having an average powder size in the range of 25 to 37 microns.

The size of the particles may also be verified using optical methods in a microscope.

According to at least one example embodiment, the diamonds in the diamond powder is artificial, or synthetic diamonds. According to at least one example embodiment, the diamonds in the diamond powder are so called real, or natural diamonds, i.e. they are formed at high temperature and pressure at depths of e.g. 140 to 190 km in the Earth's mantle.

According to at least one example alternative embodiment, the diamond powder is replaced by another incompressible and inert powder, which inert powder is incompressible and inert in relation to the hot pressing process. Such inert powder will typically have the same characteristics as described above for the diamond powder, at least that the facets of different particles in the inert powder are in contact with each other, and thus withstand compression when being subject to an external load, such as an external load stemming from the hot pressing process, and more specifically, said predetermined pressure during said predetermined time of said hot pressing process.

According to at least one example embodiment, said incompressible filler is said diamond powder, i.e. a powder comprising diamonds. In other words, according to such embodiments, the incompressible filler consists solely of diamond powder.

In some embodiments, the inert filler material is a compressible filler material and wherein said step of removing at least a part of said inert filler material comprises removing at least a part of said compressible filler material from said metal based component.

A compressible filler material differs from the incompressible filler materials discussed above in that the elements or particles making up the compressible filler material can be compressed when being subject to an external load, such as an external load stemming from the hot pressing process, and more specifically, said predetermined pressure during said predetermined time of said hot pressing process. Thus, the compressible filler material will compress and reduce the overall volume of the provided filler material during the provision of said predetermined pressure during said predetermined time of said hot pressing process. However, the compressible filler should only be compressible to a certain degree, and be able to reach its fully compressed state upon provision of said predetermined pressure during said predetermined time of said hot pressing process. The amount of compressible filler provided during the filling of the void should be chosen such that, in the fully compressed state, the compressible filler covers the protrusion element. Once the compressible filler has been compressed to its fully compressed state, it will act as a pressure delivery medium upon the protrusion element and the substrate.

In some embodiments, the compressible filler material is a ceramic filler material and wherein said step of removing at least a part of said compressible filler material comprises removing at least a part of said ceramic filler material from said metal based component, said ceramic filler material comprising at least one selected from MgO, CaO, $Al_2O_3$ and SiC.

The exemplified ceramic materials are advantageous in that they are leachable by mild acids. Thus, the step of removing the inert filler material may further comprise leaching the compressible filler material by an acid, preferably a mild acid such as acetic acid. MgO and CaO are particularly advantageous in that the product from such leaching is environmentally friendly.

In some embodiments, the second portion of the protrusion element comprises at least one extending member extending from the second portion in a direction substantially parallel to the extension of said substrate.

The method is particularly advantageous in that it provides an even pressure distribution which allows for the manufacture of metal based components having at least one protrusion having a complex geometry. The inert filler material provides a counter-pressure which allows complex geometries to be joined to the substrate without breaking and/or deforming the complex structures.

In some embodiments, the substrate comprises a plurality of cavities, and wherein the method further comprises the providing of a corresponding number of metal based protrusion elements comprising a first portion and a second portion, wherein the first portions has a shape that conforms to the shape of at least one of the plurality of cavities. The cavities may preferably have the same shape, such as blind holes. The second portions of the protrusion elements may have the same size and shape, but may also have different sizes and shapes.

In some embodiments, the material of the metal based substrate and/or the protrusion element are/is selected from a wrought material, a cast material, a sintered material and/or a material obtainable by additive manufacturing. The metal based substrate and the protrusion element may be of the same or different materials.

In some embodiments, the material of the metal based substrate is a different material than the material of the protrusion element.

In some embodiments, the second part of the protrusion element comprises a cubic shape, a hook-like shape, a barb-like shape, a tapered shape, a threaded portion, a ball joint, a mushroom shape, a rack-like shape, a tube-like shape, a spring-like shape, a screw-like shape, a rack-like shape, a lattice-like shape and/or a flange.

The present invention is compatible with any shape of the second part of the protrusion element that can be fitted into the canister and be covered by said inert filler material.

In some embodiments, the inert filler material comprises powder, beads and/or prills, and wherein said inert filler material has flow properties allowing it to be poured into and/or out of said void.

The inert filler material may be a particulate material. The particle size disclosed above in relation to the diamond particles is applicable also for the other inert filler materials disclosed herein.

According to a second aspect of the present invention, there is provided a metal based component comprising at least one protrusion on a first surface of the metal based component, wherein said metal based component comprises a body formed by a metal based substrate comprising a cavity, and at least one metal based protrusion element having a first portion arranged in said cavity, and a second portion at least partially forming said protrusion, wherein at least one inner surface of the cavity and an outer surface of the first portion of the protrusion element have metallurgically bonded to each other during a hot pressing process for a predetermined time at a predetermined pressure and a predetermined temperature, wherein said metal based component comprises metallurgical detectable traces of said substrate and protrusion element, wherein said metallurgical detectable traces are formed by crystallographic mismatch at interfaces between the substrate and the protrusion element.

Hereby, a strong metal based component with a high density and with relatively low residual stresses, having a protrusion, wherein a metallurgical bond is formed between the protrusion element and the substrate. Thus, the first portion of the protrusion element will be metallurgically bonded to at least one inner surface of the cavity. The second portion will the protrude from the surface of said substrate.

In some examples, the substrate is a monolithically substrate comprising a cavity.

Effects and features of this second aspect of the present inventive concept are thus largely analogous to those described above in connection with the first aspect of the inventive concept. Embodiments mentioned in relation to the first aspect of the present inventive concept are largely compatible with the second aspect of the inventive concept.

According to at least one example embodiment, the metallurgical detectable traces are significant of the bonding of the inner surfaces of the cavity to the outer surface of the first portion of the protrusion during the hot pressing process (e.g. HIPping process), i.e. during the process of a hot pressing for a predetermined time at a predetermined pressure and a predetermined temperature. For example, the former interface between an inner surface of the cavity and an outer surface of the first portion of the protrusion element, may be traced as the trace appears as a straight line, along which line metal grains is arranged. Hence, the term trace may be interpreted as the traceable formation of residues or residuals of the former interfaces.

According to at least one example of the invention the traces mentioned above is made visible through etching of a cross-sectional sample of the metal based component.

According to some example, the metal based component comprises a plurality of protrusions. The protrusions may be arranged on a surface of the metal based protrusion in ordered pattern comprising rows and columns.

In some embodiments the whole surface of the metal based component comprising said protrusion is diamond coated. The metal based component has preferably been coated by the method according to the first aspect of the inventive concept. In the method, a first diamond particle or grain in the diamond powder will not bond to another diamond particle or grain in the diamond powder during the hot pressing process. Consequently, each diamond grain or particle in the diamond coating does not bond to another diamond grain or particle in the diamond coating. This is advantageous in that reduces the risk of the diamond coating flaking off, which is common problem associated with prior art coating due to the fact that diamond grains may only be bonded to other adjacent diamond grains in such coatings, without being bound to the surface.

In some embodiments, said diamond coating comprises at least a first and a second layer, said first layer comprising diamond grains, said second layer comprising a carbide interlayer bonding said diamond grains to said metal-based component.

In examples, where another inert filler material has been used, the whole surface of said metal based component comprising said protrusion may comprise a coating of said inert filler material.

BRIEF DESCRIPTION OF THE DRAWINGS

The above objects, as well as additional objects, features and advantages of the present inventive concept, will be more fully appreciated by reference to the following illustrative and non-limiting detailed description of embodiments of the present invention, when taken in conjunction with the accompanying drawings, wherein.

DETAILED DESCRIPTION

In the present detailed description, embodiments of the present invention will be discussed with reference to the accompanying figures. It should be noted that this by no means limits the scope of the invention, which is also applicable in other circumstances for instance with other types or variants of methods for diamond coating a metal based component having a cavity encompassed by the scope of the claims, then the embodiments shown in the appended drawings. Further, that specific features are mentioned in connection to an embodiment of the invention does not mean that those features cannot be used to an advantage together with other embodiments of the invention.

Figure 1A:
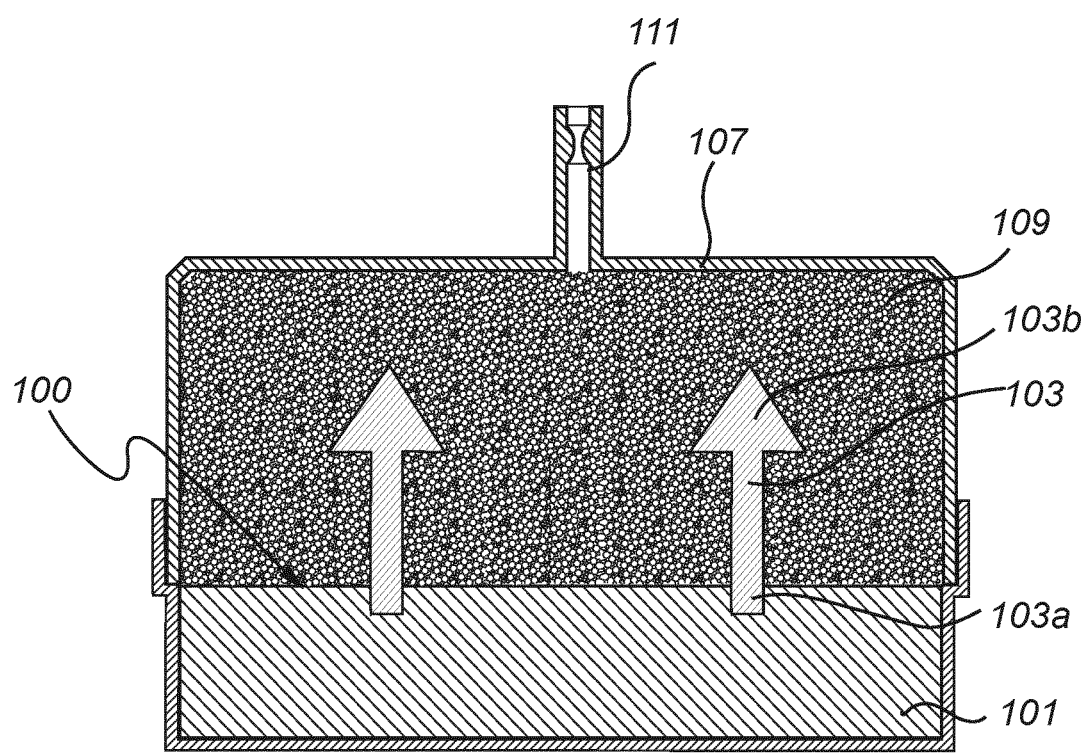
FIG. 1A shows a schematic cross-sectional view of a metal based component having at least one protrusion and an incompressible filler according to an example of the invention.

FIG. 1a shows a cross-sectional view of a metal based component 100 comprising a substrate 101 and protruding element 103 having a first portion 103a and a second portion 103b. The first portion is arranged in a cavity 105 and the second portion 103b is illustrated as having a barb-like shape. The metal based component is arranged inside a canister 107, such that a void has formed between the surface of the substrate 101 comprising the cavity and the canister 107. The void is filled, at least partly or as illustrated herein almost completely with an inert filler material 109, illustrated as a particulate filler material such as diamond powder. The flow properties of the filler material have allowed into to completely surround the protrusion elements and completely cover them. Also shown is a crimp tube 111 for removing gas from the interface between the inert filler material and the substrate.

During the hot pressing process, the first portion 103b of the protrusion element 103 is metallurgically bonded to the inner surfaces of the cavity. The inert filler material 109 acts as a pressure delivery medium which distributes the pressure on the protrusion element 103 such that complex shapes and/or geometries does not deform or break upon pressing. Herein, this is illustrated in that the filler material 109 is in contact with the second portion 103a of the protrusion element 103 over the whole outer surface of the second portion 103a, also in the areas underneath the head of the barb-like shape. Furthermore, the inert filler material 109 covers the protrusion elements 103 and prevents them from contacting the canister 107 under the hot pressing process.

Figure 1B:
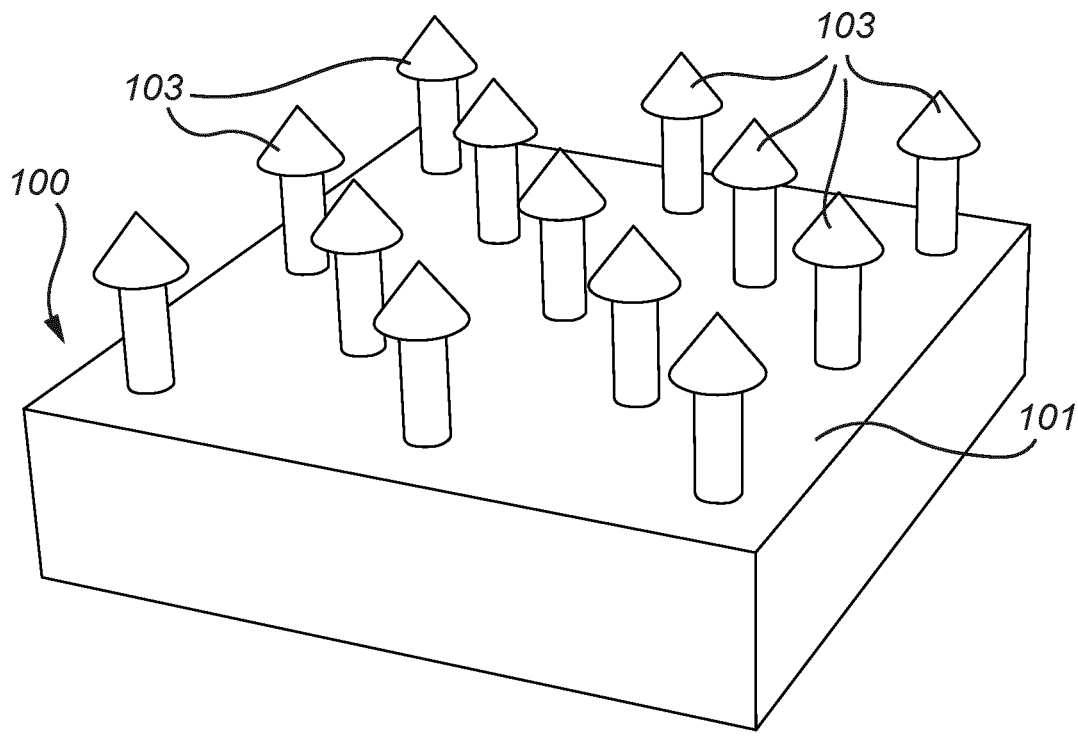
FIG. 1B shows a metal based component comprising at least one protrusion according to an example of the invention.

FIG. 1b shows schematic illustration of a metal based component 100 comprising a number of protrusions 103. A first portion, illustrated herein with a cylindrical shape, has metallurgically bonded to a corresponding cavity. In the example shown herein, the metal based component is shown with thirteen protrusions 103 arranged in a pattern on the surface of the substrate 101.

Figure 1C:
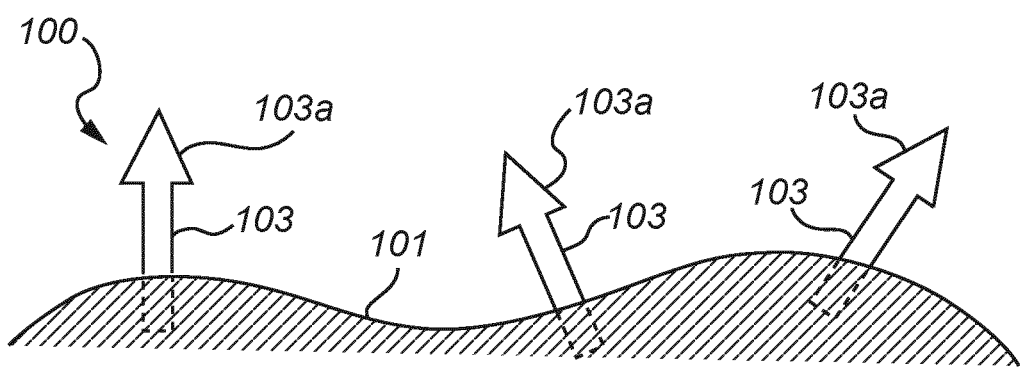
FIG. 1C shows a metal based component comprising at least one protrusion according to an example of the invention.

FIG. 1c shows schematic illustration of a metal based component 100 comprising a number of protrusions 103. A first portion, illustrated herein with a cylindrical shape, has metallurgically bonded to a corresponding cavity. In the example shown herein, the surface of the substrate 101 has a wavy shape.

Figure 2:
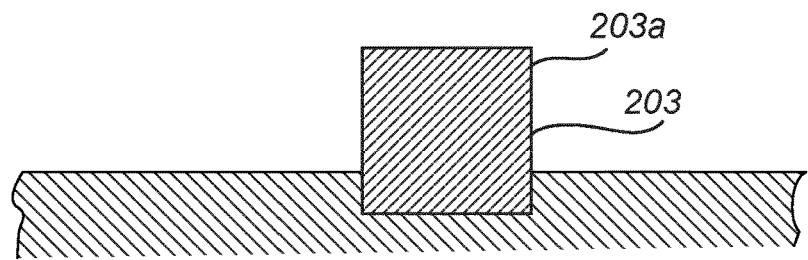
FIGS. 2-17 shows various examples of protruding elements according to examples of the invention

FIG. 2 shows a cross sectional view of an example where the second portion 203a of the protrusion 203 has a cylindrical shape.

Figure 3:
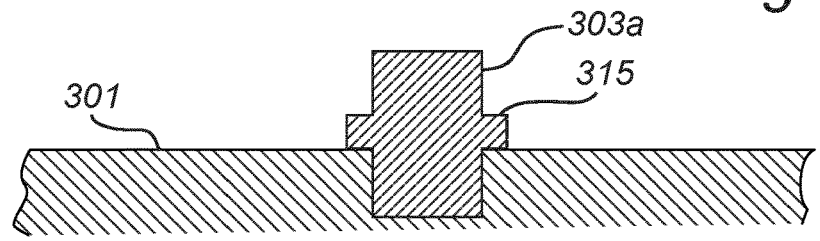

FIG. 3 shows a cross sectional view of an example where the second portion 303a of the protrusion 303 has a cylindrical shape and further comprises a flange 315, arranged level with the surface of the substrate 301.

Figure 4:
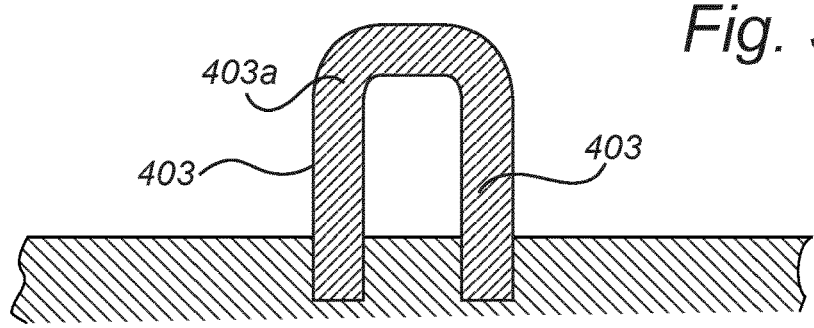

FIG. 4 shows a cross sectional view of an example wherein two adjacent protrusions 403 are shares a common second portion 403b, which allows the two adjacent protrusions 403 to form an eye hook-like shape.

Figure 5:
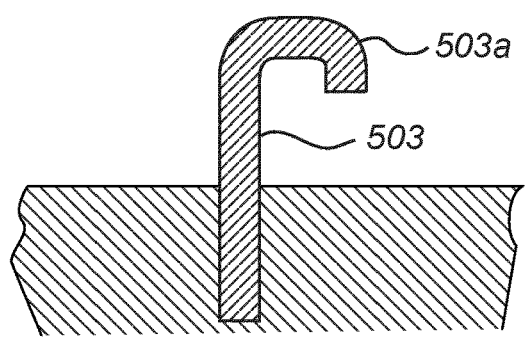

FIG. 5 shows a cross sectional view of an example where the second portion 503a of the protrusion 503 has a hook-like shape.

Figure 6:
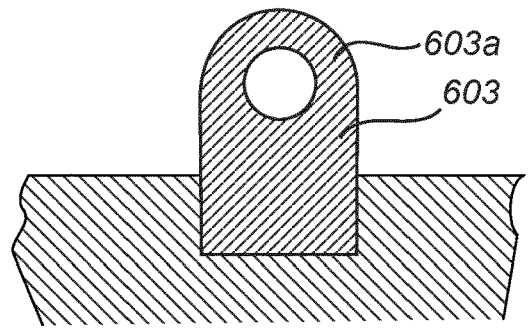

FIG. 6 shows a cross sectional view of an example where the second portion 603a of the protrusion 603 has a hook-like shape.

Figure 7:
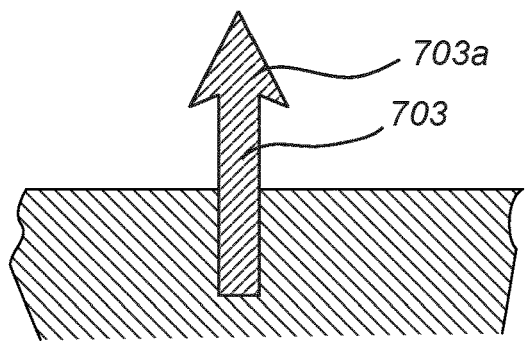

FIG. 7 shows a cross sectional view of an example where the second portion 703a of the protrusion 703 has a barb-like shape, similar to the shape illustrated in FIGS. 1a and 1b.

Figure 8:
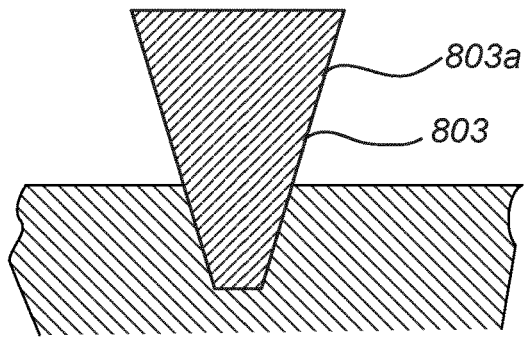

FIG. 8 shows a cross sectional view of an example where the second portion 803a of the protrusion 803 has a tapered shape, such as the shape of a truncated cone.

Figure 9:
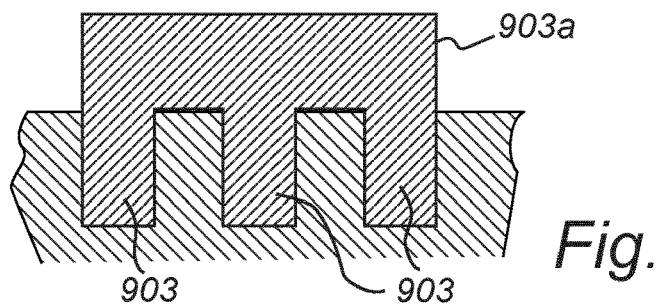

FIG. 9 shows a cross sectional view of an example where three adjacent protrusions 903 shares a common second portion 903a of the protrusions 903, which then forms a multi-legged protrusion.

Figure 10:
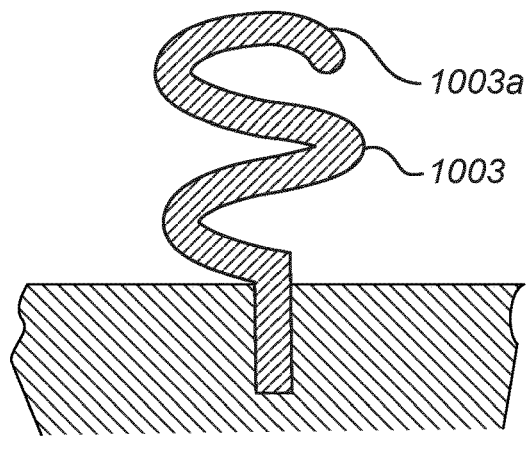

FIG. 10 shows a cross sectional view of an example where the second portion 1003a of the protrusion 1003 has a spring-like shape.

Figure 11:
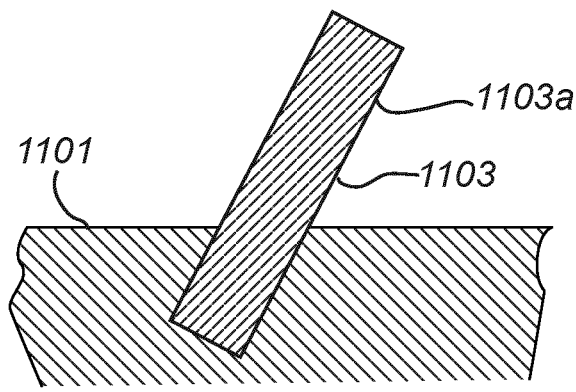

FIG. 11 shows a cross sectional view of an example where the second portion 1103a of the protrusion 1103 has a cylindrical shape. The example shown in FIG. 11 differs from the one shown in FIG. 2 in that the protruding element 1103 is positioned in the substrate at an angle with regard to the surface of the substrate 1101.

Figure 12:
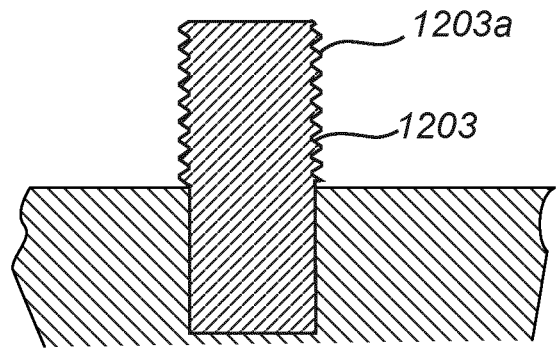

FIG. 12 shows a cross sectional view of an example where the second portion 1203a of the protrusion 1203 has a cylindrical shape comprising a threaded portion.

Figure 13:
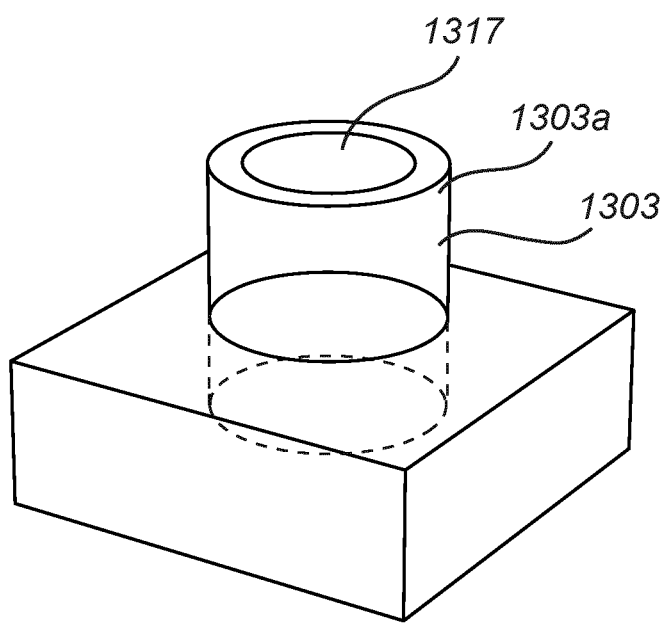

FIG. 13 shows a cross sectional view of an example where the second portion 1303a of the protrusion 1303 has a tube like shape, i.e. comprising a cavity 1317.

Figure 14:
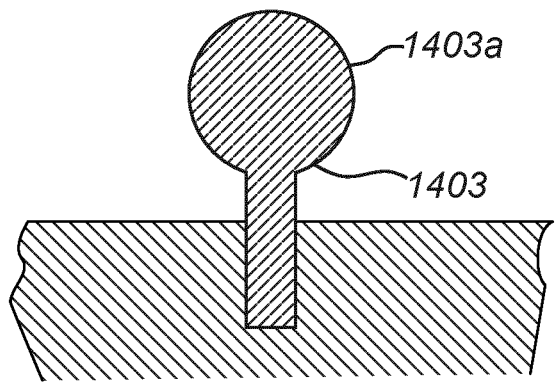

FIG. 14 shows a cross sectional view of an example where the second portion 1403a of the protrusion 1403 has a ball-joint shape.

Figure 15:
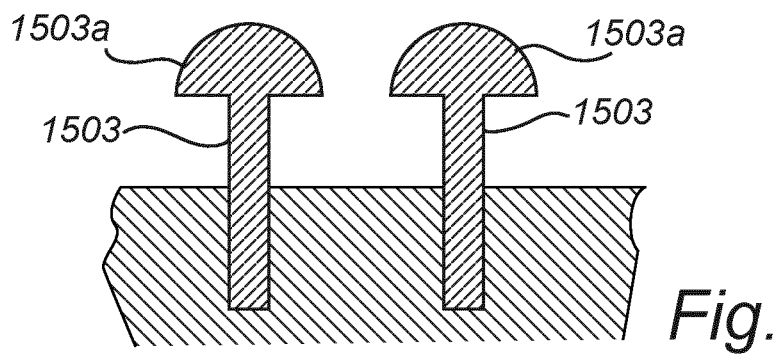

FIG. 15 shows a cross sectional view of an example where the second portion 1503a of the protrusion 1503 has a mushroom-like shape.

Figure 16:
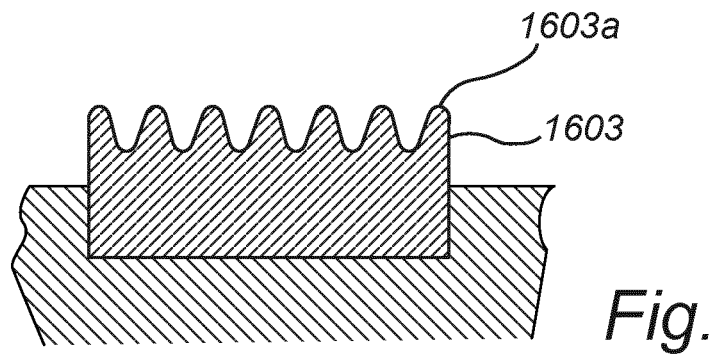

FIG. 16 shows a cross sectional view of an example where the second portion 1603a of the protrusion 1603 has a rack-like shape, configured to be engaged by a pinion for actuation purposes.

Figure 17:
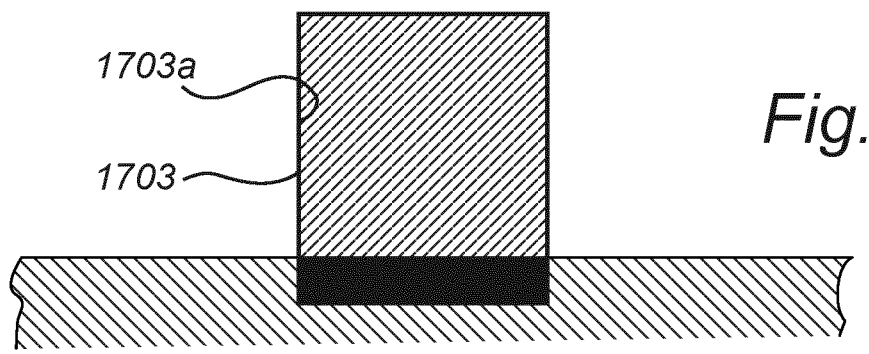

FIG. 17 shows a cross sectional view of an example where the second portion 1703a of the protrusion 1703 has a lattice-like shape. The lattice like shape may be produced by means of additive manufacturing, such as 3D printing.

Figure 18A:
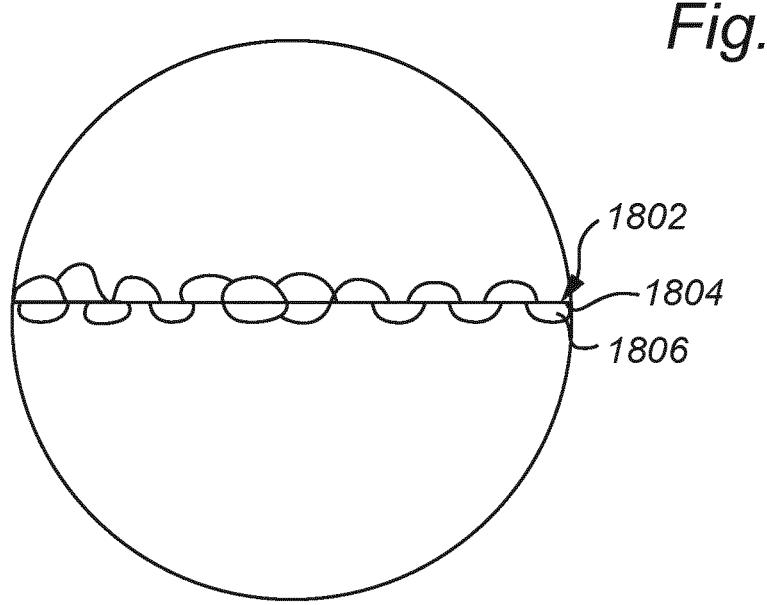
FIG. 18A shows schematic view of a metal based component comprising a protrusion.

FIG. 18A shows a shows a schematic view of a metal based component 1800. when examining a cross-section of said metal based component by microscope, a trace 1802 of former interfaces between the first portion of the protrusion element and the outer surface of the cavity is visible. The trace 1802 is typically a line 1804, along which line a crystallographic mismatch of metal grains 1806 is arranged (in the enlarged view in FIG. 17A, a trace from the interlayer interface between the protrusion element and the substrate is shown).

Figure 18B:
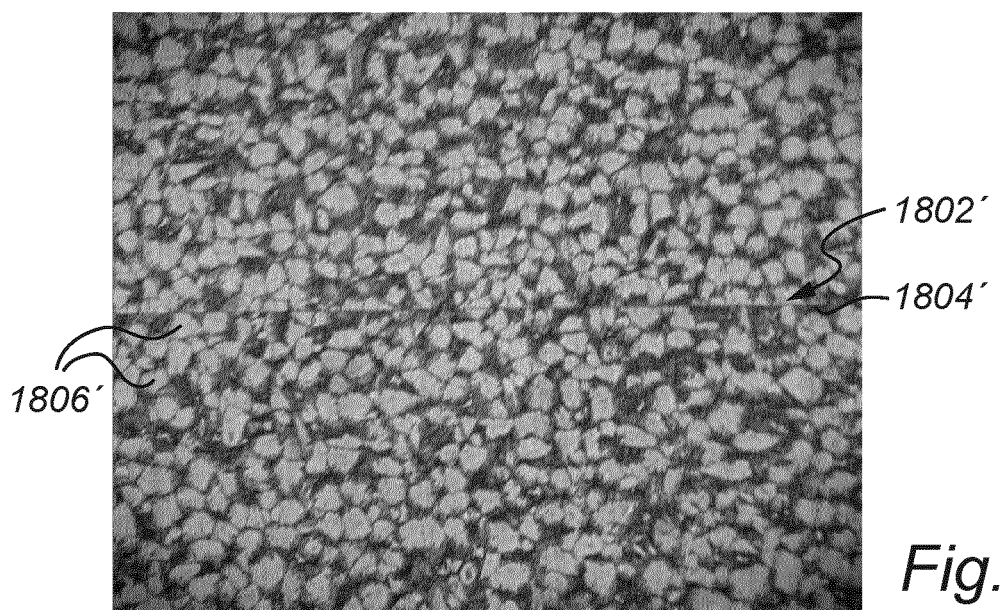
FIG. 18B shows a micrograph of a trace in a metal based component in accordance with at least one example embodiment of the invention.

FIG. 18B shows a micrograph of a trace 1802' of the interface between two of the plurality of metal based sheets, which trace is visible in the metal based compound after it is manufactured. In the micrograph, the line 1804', along which line a crystallographic mismatch of metal grains 1806' is clearly visible.

Figure 19:
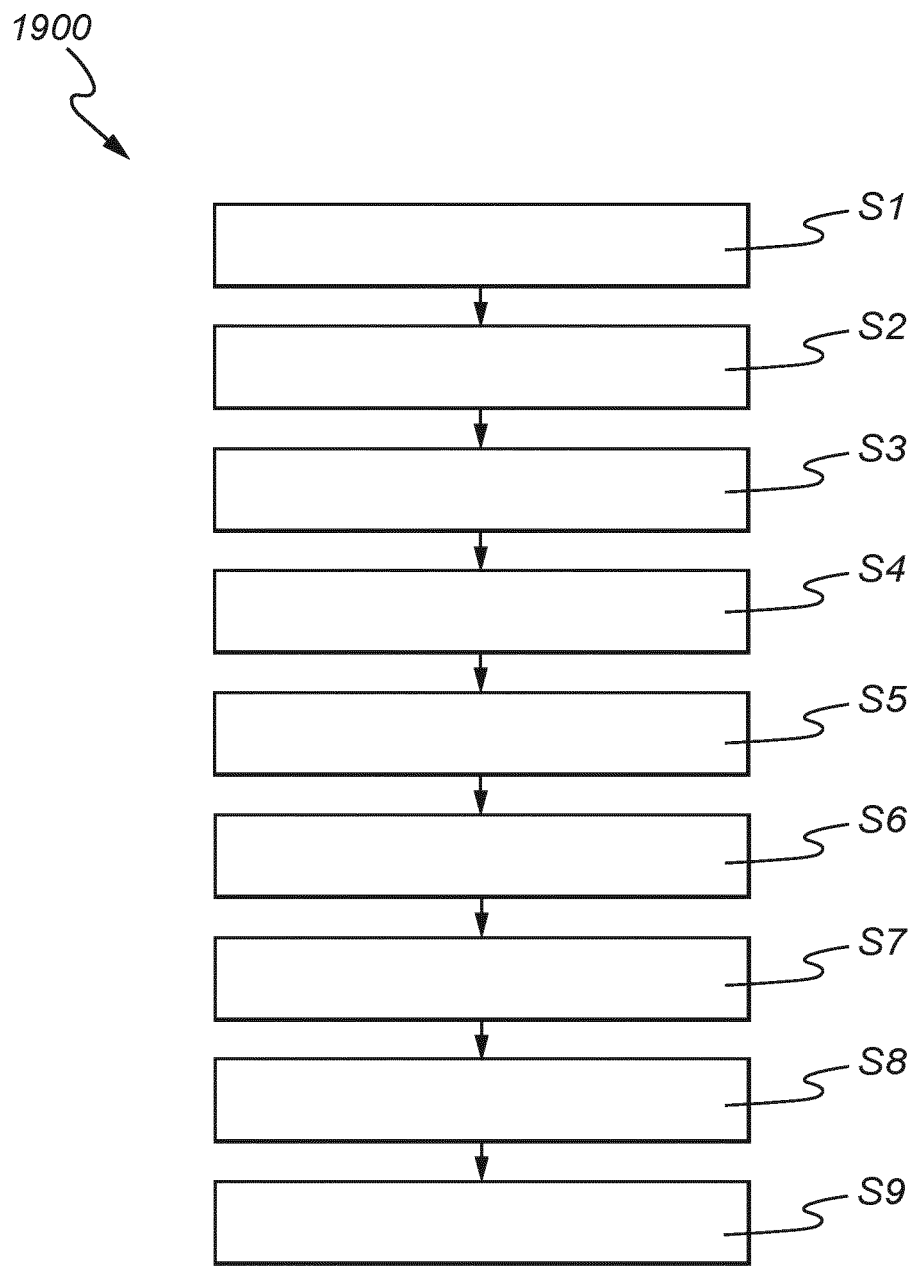
FIG. 19 shows a flow-chart explaining the steps of a method in accordance with at least one embodiment of the invention.

Turning to FIG. 19 showing a flow chart of the steps in a method 1900 for manufacturing a metal based component having a protrusion, according to at least one embodiment of the inventive concept. The metal based component comprising a protrusion of FIGS. 1a and 1b are examples of the result of the method described in relation to FIG. 18. Reference numerals used to describe structures and features of in FIGS. 1a and 1b will used when describing the method 1900 of FIG. 19.

The method 1900 comprises the steps of (steps are abbreviated with the capital "S"):

S1: providing a metal based substrate 101 comprising a surface having at least one cavity 105;

S2: providing a metal based protrusion element 103 comprising a first portion 103b and a second portion 103a, wherein said first portion 103b has a shape that conforms to a shape of the cavity 105;

S3: arranging the first portion 103b of the protrusion element 103 in said cavity 105 such that at least the second portion 103a of the protrusion element 103 protrudes from a surface of the metal based substrate 101, to form a substrate comprising a protrusion;

S4: placing said substrate comprising a protrusion in a canister 107 such that a void 115 is formed between the canister 109 and the surface 113 of the substrate comprising protrusion;

S5: filling at least a portion of the void 115 with an inert filler material 109 such that the surface 113 of the substrate comprising the protrusion is covered by the inert filler material.

In step S5, the filling may be performed by pouring the inert filler material, preferably an inert particulate filler material, into the canister 107 to at least partially fill the void 115.

The melting point of the inert filler material should be higher than then the predetermined temperature used in step S7 below.

S6: removing gas from the interface between said inert filler material 109 and said surface 113 of the substrate comprising the protrusion.

In step S6, gas is preferably removed through the crimp tube 114, which is sealed off after gas removal.

S7: subjecting said substrate comprising the protrusion to a hot pressing process for a predetermined time at a predetermined pressure and a predetermined temperature such that said substrate and protrusion element bond metallurgically to each other to form said metal based component comprising said at least one protrusion.

S8: removing at least a part of said inert filler material 109 from said metal based component having a protrusion 100. The inert filler material 109 may be removed by opening the canister 107 and pouring off the excess inert filler material 109, and/or by means of chemical leaching using an acid.

The person skilled in the art realizes that the present invention by no means is limited to the embodiments described above. The features of the described embodiments may be combined in different ways, and many modifications and variations are possible within the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements.

The invention claimed is:

1. A method for manufacturing a metal based component comprising at least one protrusion, said method comprising:
    providing a metal based substrate comprising a surface having at least one cavity;
    providing a metal based protrusion element comprising a first portion and a second portion, wherein said first portion has a shape that conforms to a shape of the cavity;
    arranging the first portion of the protrusion element in said cavity such that at least the second portion of the protrusion element protrudes at least 5 mm from the surface of the metal based substrate, to form a substrate comprising a protrusion;
    placing said substrate comprising the protrusion in a canister such that a void is formed between the canister and the surface of the substrate comprising the protrusion;
    filling at least a portion of the void with a diamond powder such that the surface of the substrate comprising the protrusion is covered by the diamond powder;
    removing gas from the interface between said diamond powder and said substrate comprising the protrusion;
    subjecting said substrate comprising the protrusion to a hot pressing process for a predetermined time at a predetermined pressure and a predetermined temperature such that said substrate and protrusion element bond metallurgically to each other to form said metal based component comprising said at least one protrusion; and
    removing at least a part of said diamond powder from said metal based component having a protrusion;
    wherein the melting point of the diamond powder at said predetermined pressure is higher than said predetermined temperature.

2. The method according to claim 1, wherein said arranging the first portion of the metal based protrusion element in said cavity such that the second portion of the protrusion element protrudes from a surface of the first metal based substrate further comprises arranging said first portion to fit snugly inside said cavity, such that the diamond powder is prevented from entering said cavity, and wherein, after said filling, substantially a whole outer surface of the second portion of said protrusion element is in contact with the diamond powder.

3. The method according to claim 2, wherein said first portion has a cylindrical or quadrangular shape and wherein said cavity has a shape of a cylindrical or quadrangular hole.

4. The method according to claim 1, wherein the average grain size of said diamond powder is at least 1 µm, or at least 10 µm, or at least 20 µm, or at least 30 µm and/or wherein the average grain size of said diamond powder is at most 1000 µm or at most 500 µm, or at most 250 µm, or at most 100 µm, or at most 50 µm, or at most 40 µm.

5. The method according to claim 1, wherein the second portion of the protrusion element comprises at least one extending member extending from the second portion in a direction substantially parallel to the extension of said substrate.

6. The method according to claim 1, wherein the substrate comprises a plurality of cavities, and wherein the method further comprises the providing of a corresponding number of metal based protrusion elements comprising a first portion and a second portion, wherein the first portion has a shape that conforms to the shape of at least one of the plurality of cavities.

7. The method according to claim 1, wherein the material of the metal based substrate and/or the protrusion element are/is selected from a wrought material, a cast material, a sintered material and/or a material obtainable by additive manufacturing.

8. The method according to claim 7, wherein the material of the metal based substrate is a different material than the material of the protrusion element.

9. The method according to claim 1, wherein the second part of the protrusion element comprises a cubic shape, a hook-like shape, a barb-like shape, a tapered shape, a threaded portion, a ball joint, a mushroom shape, a rack-like shape, a lattice shape, a fastening element and/or a flange.

10. The method according to claim 1, wherein said diamond powder has flow properties allowing it to be poured into and out of said void.

11. The method according to claim 1, wherein the predetermined time may be within the range of 1 hour to 12 hours, the predetermined pressure may be within the range of 10 MPa to 200 MPa, and the predetermined temperature may be within the range of 500° C. to 2000° C.

12. The method according to claim 1, wherein the surface of the formed metal based component comprising said protrusion is diamond coated.

* * * * *